(12) United States Patent
Van Der Mark et al.

(10) Patent No.: US 11,471,025 B2
(45) Date of Patent: Oct. 18, 2022

(54) OPTICAL CONNECTION DEVICE AND METHOD

(71) Applicant: KONINKLIJKE PHILIPS N.V., Eindhoven (NL)

(72) Inventors: Martinus Bernardus Van Der Mark, Best (NL); Paulus Rene Maria Van Beers, Eindhoven (NL); Antonius Wilhelmus Maria De Laat, Den Dungen (NL); Eibert Gerjan Van Putten, 'S-Hertogenbosch (NL); Hendrikus Antonius Cornelus Compen, Budel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 146 days.

(21) Appl. No.: 16/650,569

(22) PCT Filed: Sep. 21, 2018

(86) PCT No.: PCT/EP2018/075587
§ 371 (c)(1),
(2) Date: Mar. 25, 2020

(87) PCT Pub. No.: WO2019/063428
PCT Pub. Date: Apr. 4, 2019

(65) Prior Publication Data
US 2020/0221934 A1    Jul. 16, 2020

(30) Foreign Application Priority Data
Sep. 28, 2017   (EP) .................................... 17193647

(51) Int. Cl.
*A61B 1/00* (2006.01)
*A61B 1/07* (2006.01)
*G02B 6/38* (2006.01)

(52) U.S. Cl.
CPC ........ *A61B 1/00126* (2013.01); *A61B 1/0011* (2013.01); *A61B 1/00128* (2013.01); *A61B 1/07* (2013.01); *G02B 6/3807* (2013.01)

(58) Field of Classification Search
CPC .............. A61B 1/00126; A61B 1/0011; A61B 1/00128; A61B 1/07; G02B 6/3807
See application file for complete search history.

(56) References Cited

U.S. PATENT DOCUMENTS 3,612,483 A * 10/1971 Pool .......................... F16K 1/36
                                                                  251/306
4,146,019 A *  3/1979 Bass ......................... A61B 1/12
                                                                  600/108
(Continued)

FOREIGN PATENT DOCUMENTS

CA          2721715         11/2009
DE   202012005202 U1 *  6/2012   ........... H02G 3/0675
(Continued)

OTHER PUBLICATIONS

International Search Report and Written Opinion dated Jan. 2, 2019 for International Application No. PCT/EP2018/075587 Filed Sep. 21, 2018.

*Primary Examiner* — Peter Radkowski

(57) ABSTRACT

The present invention relates to an optical connection device for optically connecting a first connector (42) of a first optical fiber device (44) with a second connector (46) of a second optical fiber device (48) along an optical axis, which comprises a plug part (40) having an elongated shaft (58) having a longitudinal shaft axis (62) and a lumen (60) extending through the shaft (58) along the shaft axis (62) for receiving the first connector (42), the plug part (40) further having a cap (64) at a first end of the shaft (58) which has an insertion opening (66) for insertion of the first connector (42) into the lumen (60), the opening (66) being aligned and (Continued)

communicating with the lumen (60), the plug part (40) having an optical window (68) having a solid body element (69), wherein the plug part (40) is at least in part deformable; and a clamp part (18), wherein the plug part (40) is configured to be at least partially inserted into the clamp part (18), and the clamp part (18) is configured to, when the plug part (40) is at least partially inserted in the clamp part (18) and when the first connector (42) is inserted into the lumen (60) of the shaft (58) of the plug part (40), exert a force onto the plug part (40) which deforms the plug part (40) upon tightening the clamp part (18) so as to clamp and hold the first connector (42) in position and orientation with respect to the optical axis.

20 Claims, 6 Drawing Sheets

(56) References Cited

U.S. PATENT DOCUMENTS

| | | | | |
|---|---|---|---|---|
| 4,577,870 A * | 3/1986 | Scott | ............ | F16J 15/32 |
| | | | | 137/625.69 |
| 4,607,911 A * | 8/1986 | Rhodes | ............ | G02B 6/3831 |
| | | | | 385/136 |
| 5,203,534 A * | 4/1993 | Demarest | ............ | B05B 7/12 |
| | | | | 222/479 |
| 5,283,850 A * | 2/1994 | Souloumiac | ............ | G02B 6/2848 |
| | | | | 385/66 |
| 5,300,067 A * | 4/1994 | Nakajima | ............ | A61C 1/0046 |
| | | | | 606/16 |
| 5,329,936 A * | 7/1994 | Lafferty | ............ | A61B 1/00096 |
| | | | | 600/109 |
| 5,371,814 A * | 12/1994 | Ames | ............ | G02B 6/32 |
| | | | | 385/25 |
| 5,374,245 A * | 12/1994 | Mahurkar | ............ | A61M 25/001 |
| | | | | 604/43 |
| 5,455,880 A * | 10/1995 | Reid | ............ | G02B 6/3834 |
| | | | | 385/87 |
| 5,949,929 A * | 9/1999 | Hamm | ............ | G02B 6/3604 |
| | | | | 385/25 |
| 6,139,194 A * | 10/2000 | Bella | ............ | G02B 6/382 |
| | | | | 362/551 |
| 6,373,048 B1 * | 4/2002 | Tschanun | ............ | G01C 19/721 |
| | | | | 250/231.12 |
| 6,374,245 B1 * | 4/2002 | Park | ............ | G06F 16/10 |
| 6,847,770 B2 * | 1/2005 | Kittaka | ............ | C03C 21/002 |
| | | | | 385/124 |
| 7,031,567 B2 * | 4/2006 | Grinderslev | ............ | G02B 6/32 |
| | | | | 385/34 |
| 8,678,009 B2 * | 3/2014 | Hagn | ............ | A61B 46/10 |
| | | | | 128/852 |
| 8,740,878 B2 * | 6/2014 | Heaton | ............ | A61M 1/73 |
| | | | | 604/543 |
| 9,408,527 B2 * | 8/2016 | Hoeg | ............ | A61B 1/00179 |
| 9,636,005 B2 * | 5/2017 | Yoshino | ............ | A61B 1/0684 |
| 9,636,493 B2 * | 5/2017 | Chung | ............ | A61M 39/105 |
| 9,658,407 B2 | 5/2017 | Volker | | |
| 9,804,339 B2 | 10/2017 | Fukuoka | | |
| 10,299,661 B2 * | 5/2019 | Van Putten | ............ | G02B 6/32 |
| 2006/0235436 A1 * | 10/2006 | Anderson | ............ | A61B 34/30 |
| | | | | 606/130 |
| 2010/0329609 A1 * | 12/2010 | Shimotsu | ............ | G02B 6/32 |
| | | | | 385/50 |
| 2011/0184244 A1 * | 7/2011 | Kagaya | ............ | A61B 1/00128 |
| | | | | 600/182 |
| 2016/0038030 A1 * | 2/2016 | Smith | ............ | A61B 5/7278 |
| | | | | 600/427 |
| 2017/0082806 A1 * | 3/2017 | Van Der Mark | .... | G02B 6/3871 |
| 2018/0264239 A1 * | 9/2018 | Piskun | ............ | A61B 90/02 |

FOREIGN PATENT DOCUMENTS

| | | | | |
|---|---|---|---|---|
| GB | 2483154 | | 2/2012 | |
| JP | 2005111100 A | * | 4/2005 | ............ A47C 27/148 |
| JP | 4577870 B2 | * | 11/2010 | ............ A47C 27/15 |
| WO | 2015/150149 | | 10/2015 | |
| WO | 2016/081286 | | 5/2016 | |
| WO | 2016/083189 | | 6/2016 | |
| WO | 2016/193051 | | 12/2016 | |

\* cited by examiner

OPTICAL CONNECTION DEVICE AND METHOD

CROSS REFERENCE TO RELATED APPLICATIONS

This application is the U.S. National Phase application under 35 U.S.C. § 371 of International Application No. PCT/EP2018/075587 filed Sep. 21, 2018, published as WO 2019/063428 on Apr. 4, 2019, which claims the benefit of European Patent Application Number 17193647.9 filed Sep. 28, 2017. These applications are hereby incorporated by reference herein.

FIELD OF THE INVENTION

The present invention relates to the field of connecting optical fiber devices with one another. The invention finds applications in interventional medical devices and interventional treatment procedures, in particular in minimally invasive medical procedures using optical interrogation techniques.

BACKGROUND OF THE INVENTION

In minimally invasive medical interventions, guidewires are used for advancing catheters to a target region (e.g., a guidewire for advancing a catheter to a heart during a minimally invasive cardiovascular intervention). These procedures are generally guided with, for example, real-time X-ray imaging, which depicts two-dimensional projection images of the catheters and guidewires. However, challenges with X-ray imaging include the 2D nature of the imaging and the ionizing radiation to the patient and physician. A more viable alternative is using optical shape sensing technology, which may provide full three-dimensional shape information of medical devices without the need for any harmful radiation. One way to implement spatially sensitive bend and twist sensing using optical fibers is to combine multiple fiber cores having fiber-Bragg gratings along their length. One potential set-up may be three or more fiber cores oriented in a helical structure along the longitudinal fiber axis including an additional straight fiber core in the helix center. Specifically, optical shape sensing enabled guidewires are used in minimally invasive procedures which have optical connectors at their proximal end for facilitating a backloading of catheters over the proximal end of the guidewires. The guidewire may be advanced to a target region of the intervention prior to the introduction of the diagnostic or therapeutic catheter. The guidewire is typically a thin wire with specifically designed material properties that facilitates a loading of the catheter over a proximal end of the guidewire and an advancement of the catheter over the guidewire to reach the target region.

In the cases where guidewires are needed to reach the target region prior to advancing the catheter, it would be desirable to use the shape sensing capabilities during the guidewire advancing phase prior to the backloading of the catheter. However, in order to use the guidewire with the shape sensing capability, it needs to be connected to an optical system, e.g. an optical interrogator console, via an optical connector at the point where the backloading would normally occur. In order to allow backloading, optical connectors for guidewires are required which are small enough to allow standard catheters to be backloaded onto the guidewire prior to reestablishing the optical connection for continued shape sensing of the guidewire.

For backloadable guidewires, optical connectors have been proposed which comprise one or more graded index (GRIN) lenses, as, for example, described in WO 2016/193051 A1. GRIN lenses are a promising choice as an optical component in optical connectors because of their compactness and their intrinsically low surface reflection. In an ordinary lens, focusing of light relies on refraction of the light on its entrance and exit surfaces due to the difference in refractive index in the axial direction (the general direction of light propagation). In a GRIN lens this is different. The GRIN lens has a radial refractive index profile that makes that, within its working range, (given by the aperture and numerical aperture), light is bent, within the lens, towards the optical axis (this means the light is focused). The implication is that for GRIN lenses focusing can occur without any axial variation in the refractive index and hence that there are no reflections of light at any axial refractive index step (as would be the case for ordinary lenses). This property is used to eliminate all air to glass transitions when the connection between two optical connectors is established. The GRIN lenses are made of a length such that a set of collimated beams may enter and exit the connector to and from the focal points at the cores of the (single-mode) multi-core sensor fiber. For measuring and calculating the shape of the optical fiber some recognizable reflection is however required to be able to align, to the micron level, the relative starting positions for shape reconstruction of all of the fiber cores of the optical fiber. The relatively low, but sufficient reflections from the end facets of GRIN lenses appear to be a very useful, stable and natural choice for serving this task. A first short section of optical fiber, for example 20-40 mm, starting from the transition from the GRIN lens to the optical fiber must be kept straight (or at least in a known shape) to know the starting direction as well as the starting position for the optical sensing procedure. The connector of a backloadable guidewire is therefore dimensioned as a rather stiff rod, which may be several centimeters long.

Another problem in using backloadable guidewires is sterility. It is known from WO 2016/193051 A1 to use an optical element, for example a foil, as a sterility barrier between the connector at the proximal end of a guidewire and the connector at the distal end of a patch cord which is connected to the optical console in a non-sterile zone. For backloading procedures, it should be made sure that, when connecting the guidewire connector to the patch cord connector, the guidewire connector over which a catheter is to be backloaded, is not contaminated by the patch cord connector.

Thus, in order to protect the patient, it is required to make a sterility barrier at the connection of the first optical fiber device, e.g. a guidewire, and the counter connector of a second optical fiber device, e.g. a patch cord. The sterility barrier however, must be optically transparent and have sufficiently low optical reflections, and should transmit the light without introducing too much optical loss or aberration. To this end, active mechanical alignment of the first connector, e.g. the guidewire connector, and the second connector, e.g. the patch cord or console connector may be required.

Therefore, when making an optical connection between a first connector of a first optical fiber device and a second connector of a second optical fiber device, two tasks must be accomplished. One task consists in proper optically aligning the two connectors with respect to one another and maintaining this alignment during a procedure, e.g. a medical interventional procedure. The other task is to maintain sterility, in particular when a further interventional device is loaded over the back of the first optical fiber device and pushed forward into the patient's body. In other words, an optical connection is required which has good optical performance on the one hand and which meets the requirements of sterility on the other hand.

U.S. Pat. No. 5,283,850 discloses an optical fiber connector comprising a deformable sleeve for receiving the fiber in a rigid connector body to hold the fiber in position relative to the body. After compression, the front end of the sleeve remains set back inside the body.

SUMMARY OF THE INVENTION

It is an object of the present invention to provide an optical connection device for optically connecting a first connector of a first optical fiber device with a second connector of a second optical fiber device, which is improved in terms of both optical properties and mechanical properties as well as in terms of sterility.

It is a further object of the invention to provide a method of optically connecting a first connector of a first optical fiber device with a second connector of a second optical fiber device, which provides a sterile and optically well performing connection between the optical fiber devices.

According to an aspect of the invention, an optical connection device for optically connecting a first connector of a first optical fiber device with a second connector of a second optical fiber device along an optical axis is provided, comprising:

a plug part having an elongated shaft having a longitudinal shaft axis and a lumen extending through the shaft along the shaft axis for receiving the first connector, the plug part further having a cap at a first end of the shaft which has an insertion opening for insertion of the first connector into the lumen, the opening being aligned and communicating with the lumen, the plug part having an optical window having a solid body element which closes the interior of the shaft including the lumen against the environment, wherein the plug part is at least in part deformable; and a clamp part, wherein the plug part is configured to be at least partially inserted into the clamp part, and the clamp part is configured to, when the plug part is at least partially inserted in the clamp part and when the first connector is inserted into the lumen of the shaft of the plug part, exert a force onto the plug part that deforms the plug part upon tightening the clamp part so as to clamp and hold the first connector in position and orientation with respect to the optical axis.

The optical connection device is configured to connect a first and a second connector along an optical axis, wherein the optical axis is defined by, i.e. contains the second connector. When the connection is made, the first connector is aligned with the second connector and thus the optical axis. The optical connection device according to the invention comprises a plug part and a clamp part. The plug part is designed to receive a connector of an optical fiber device, e.g. the connector of a backloadable guidewire. The plug part has an elongated shaft which preferably is straight. The shaft of the plug part may have a length of several centimeters so that it may be well adapted to the length of typical connectors of backloadable guidewires. The plug part further has a cap which may serve as a handle when manipulating the plug part. The cap further serves to introduce the connector into the shaft of the plug part. The cap and the shaft may also provide sterility when making the connection between the two connectors. In particular, the cap of the plug part may have a dimension perpendicular to the shaft axis which may be significantly larger, e.g. 2 to 10 times larger, than the transverse dimension of the shaft. The shaft, which may be cylindrical in shape may have an outer diameter of as small as a few millimeters, for example 2 to 5 mm or even less. The elongated shaft is advantageous because it aligns the first connector with the shaft axis automatically when the connector is inserted into the shaft. Thus, any alignment problems of the connectors with respect to one another may be avoided by the optical connection device according to the invention. It may be advantageous when the connector when inserted into the shaft is rotatable about the shaft axis in order to rotationally align the first connector with respect to the second connector before the connection is fixed.

As a further sterility measure, the shaft has an optical window which may be formed by or comprise a solid body element which is optically transparent with respect to the wavelength used by the optical fiber devices. In particular, the optical window may mechanically close the lumen of the shaft between the sterile connector and the non-sterile connector, when the connection is made. The window may be arranged at an end or close to an end of the shaft opposite the cap of the plug part. A solid body element as used in embodiments herein is to be understood as an element in a solid state, which may be hard or stiff, for example a glass plate, or may be soft, in particular flexible or deformable, for example a foil or membrane.

The clamp part has the function to provide a force acting on the plug part which deforms the plug part when the plug part is inserted into the clamp part. By exerting a force upon tightening or closing the clamp part, the plug part is deformed and thereby clamps and holds the first connector in position and orientation with respect to the optical axis. The optical axis may be defined by a longitudinal symmetry, e.g. center axis of the optical connection device. It may be provided that only the shaft of the plug part is deformed when the clamp part exerts the force on the plug part, while the cap is not deformed, however the invention is not limited thereto. The clamp part may further be configured to hold the second connector in alignment with the first connector.

In total, the optical connection device according to the invention provides sufficient sterility to a connector of an optical fiber device like a guidewire, and an optical connection with improved optical properties between the connectors of the optical fiber devices.

Preferred embodiments of the invention are defined in the dependent claims.

According to a preferred embodiment, the optical connection device may be arranged to cooperate with a drape or sock configured to be arranged over the clamp part, wherein the drape or sock has a hole through which the plug part is insertable into the clamp part. When the plug part is inserted into the clamp part, the drape or sock may be sandwiched between them. The drape or sock is a further measure which may be advantageous in keeping the connector of the interventional device, e.g. guidewire, sterile. The sock may have a skirt which may go down onto an operating table in a surgical procedure. The drape, sock and skirt may provide an extended sterility barrier between, on the one hand, the connector clamp part and patient table and, on the other hand, the interventional device, e.g. guidewire, and patient.

The hole in the drape or sock preferably is smaller than the cap or a portion of the cap which is disposed in the hole of the drape or sock when the plug part is inserted into the clamp part. Further, the drape or sock may be configured to make a seal between the cap of the plug part and the clamp part. This further improves sterility by preventing non-sterile fluids to enter the interior of the plug part or clamp part so that a contact of such fluids with the connector of the interventional device is avoided. The drape or sock, together with the plug part make a barrier that separates a sterile zone for the patient and the interventional device from a non-sterile zone.

Further, it is advantageous if the lumen of the shaft is arranged on a so-called neutral line for compression of the shaft, which means that it does not shift in position under the compression forces applied by the clamp part. Typically, for compatibility and ease of manufacturing this may be a line of symmetry of the connection device, and therefore the lumen of the shaft may be arranged centrally in the shaft, wherein the shaft may have at least one elongated channel in fluid communication with the lumen. This central lumen is called, more generally, the neutral lumen and is the lumen into which the first connector is inserted.

Such one or more channels are advantageous because gases like air or liquids such as saline solution, water or blood can escape through the channel or channels, in particular when making the connection between the first connector and the second connector. Thus, pressure may not build up, but pressure is equalized at any time in the optical connection device.

The shaft may have a plurality of channels in fluid communication with the neutral lumen and arranged angularly distributed around the lumen. The channels may be part of the neutral lumen or separate therefrom.

There may be any number of channels, but more preferably eight or six or five channels in the shaft surrounding the lumen and being in fluid communication with the lumen. The channels may advantageously contribute to the deformability of the shaft of the plug part, when the clamp part exerts a force onto the plug part in order to clamp a connector in the plug part.

Preferably, the channels are angularly distributed around the neutral lumen in equidistant manner, so deformation of the shaft advantageously is rotationally symmetric, which improves holding the connector in place when the clamp part is tightened. For optimum symmetry and homogeneity of the clamping force, the clamp part may have the same number, or an integer multitude of clamping sections as there are channels in the plug part.

Further preferably, the shaft of the plug part is elastically deformable.

When the plug part is elastically deformable, the same plug can be used several times because repeated clamping and unclamping is possible without the plug part being damaged and without breaking the sterile barrier. Preferably, the material of the plug part may be sufficiently smooth to let the first connector slide in easily, but, when the clamp part is tightened and the plug part is compressed onto the first connector, the first connector should find sufficient friction with the material of the plug part.

Further, the solid body element of the window may comprise a transparent element the refractive index of which is matched with the refractive index of at least one of a first optical element of the first connector and a second optical element of the second connector.

When the window is refractive-index matched with optical elements of the first connector and/or the second connector any undesired reflections and refractions at these interfaces may be avoided.

Further, the solid body element of the window may comprise a transparent element which is elastically deformable, in particular compressible, in longitudinal direction of the lumen. When bringing the connectors of the optical fiber devices together, with the transparent element in between, some air gap may remain that will cause optical reflection. For example, a small but inevitable angle may come as a result from a polishing process of the connector ends. To overcome these geometrical differences, the transparent element is preferably made sufficiently compressive and preferably thick enough so that by establishing the connection between the connectors the transparent element may be compressed until any air gap at the interface is removed. This measure therefore may further enhance the optical performance of the optical connection device.

Further, the cap of the plug part may have a portion configured to be snap-fitted into the clamp part. When assembling the plug part and the clamp part, the plug part may be inserted into the clamp part and, in an initial state, pre-fixed by snapping or clicking into the clamp part. This facilitates manipulating the optical connection device when making the connection between the connectors. After the plug part is clicked into the clamp part, the first connector may be inserted into the plug part by sliding it into the shaft of the plug part which sliding movement is not hindered by the snap-fit seat of the plug part in the clamp part.

Further, the cap of the plug part may have a funnel or trumpet-shaped end comprising the insertion opening. A funnel or trumpet-shaped end of the cap advantageously promotes or facilitates the insertion of the first connector into the plug part.

Further, the first connector may be rotatable, when inserted into the plug part, relative to the plug part about the longitudinal axis of the plug part before the clamp part is tightened.

Further, the second connector may be rotatable relative to the plug part and first connector about the longitudinal axis Such a configuration is particularly advantageous if the connectors include multi-core optical fibers where it may be necessary to rotationally align the fiber cores of both connectors correctly. Such an alignment can be easily performed by rotating one or both of the connectors about the optical axis, e.g. the longitudinal symmetry axis of the optical connection device.

In this regard, the shaft of the plug part may have an inner guiding surface which allows sliding of the first connector in the shaft when the clamp part is not or only slightly pre-tightened, and which provides friction to hold the first connector in place when the clamp part is tightened.

Further, the optical connection device may further comprise a structure, which is configured to connect and hold the second connector of the second optic fiber device to the clamp part. The structure may be a component of the clamp part. The second connector may be pre-mounted on the clamp part before the plug part is inserted into the clamp part. Such a structure may be a socket having a bore aligned with the optical axis into which the second connector may be inserted, e.g. before the plug part is inserted into the clamp part. The clamp part may have a bore for accommodating the shaft of the plug part which is coaxial with the bore of the socket. Such a configuration further facilitates proper alignment of the connectors with respect to one another along the optical axis when making the connection.

According to a second aspect, a method of optically connecting a first connector of a first optical fiber device with a second connector of a second optical fiber device is provided, comprising:

providing a plug part having an elongated shaft with a lumen extending through the shaft, a cap at a first shaft end of the shaft which has an insertion opening, the opening being aligned and communicating with the lumen, the plug part having an optical window having a solid body element which closes the interior of the shaft including the lumen against the environment, providing a clamp part having the second connector connected thereto, inserting the plug part at least partially into the clamp part so that the window contacts the second connector at one side of the window, inserting the first connector into the plug part so that the first connector contacts the window at an opposite side, tightening the clamp part to exert a force onto the plug part so as to deform the plug part to clamp the first connector and to hold the first connector in position and orientation with respect to the second connector.

It shall be understood that the claimed method has similar and/or identical preferred embodiments as the claimed device and as defined in the dependent claims.

The method preferably further comprises, before tightening the clamp part, rotationally aligning the first connector and the second connector with respect to one another while measuring an optical signal passed through the first and second connectors.

When the first optical fiber device is an optical shape sensing enabled device, light from an optical console may be transmitted through the second optical fiber device into the first optical fiber device, and by measuring the signal strength of the light reflected back from the first optical fiber device while rotating the first connector and/or the second connector relative to one another the proper rotational alignment may be found when the signal strength of the back-reflected light is maximum.

Preferred embodiments of the invention are defined in the dependent claims. It shall be understood that the claimed method has similar and/or identical preferred embodiments as the claimed device as described herein.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
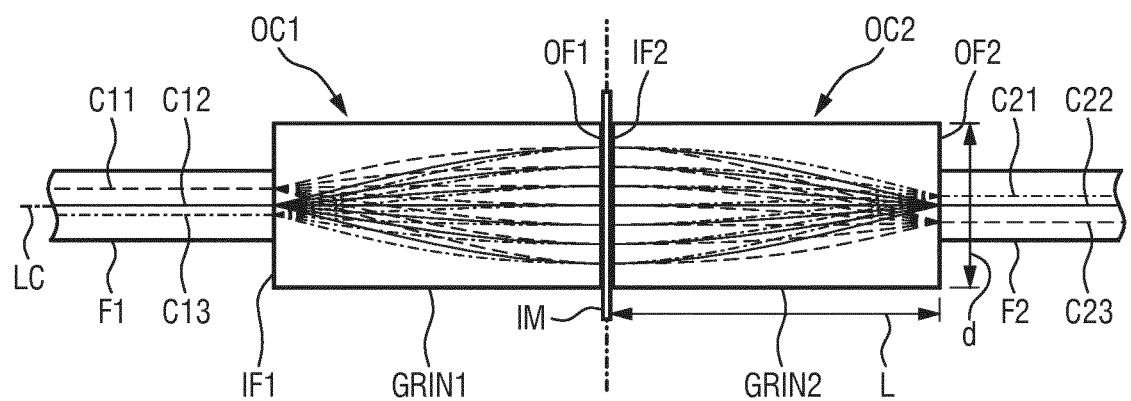
FIG. 1 shows two GRIN lenses in a side view connected to multi-core optical fibers for use in connectors of optical fiber devices.

Before embodiments of optical connection devices for optically connecting connectors of optical fiber devices with one another, a general explanation of connectors having GRIN lenses will be given with reference to FIG. 1. FIG. 1 shows an optical connector OC1 and a counter optical connector OC2. The optical connector OC1 comprises an optical fiber F1 and a GRIN lens GRIN1. The optical fiber F1 may extend through a guidewire in order to sense the optical shape of the guidewire in an interventional procedure. The optical fiber F1 may be a multi-core fiber having fiber cores C11, C12, C13 or more fiber cores, wherein the fiber core C12 is a central core with respect to the longitudinal center axis LC of the fiber F1.

Light beams from each of the fiber cores C11, C12, C13 enter the GRIN lens GRIN1 at an end facet IF of the GRIN lens GRIN1 and exit the GRIN lens GRIN1 at an end facet OF of the GRIN lens GRIN1 as collimated light beams. The collimation effect of the GRIN lens GRIN1 is due to the pitch of ¼ of the GRIN lens GRIN1 as known to a person skilled in the art. The collimated light beams then enter the optical connector OC2 having a GRIN lens GRIN2 and an optical fiber F2 which may be included in a patch cord connected, for example, to an optical interrogator console used in optical shape sensing procedures.

It is to be noted that a light beam coming from fiber core C11 enters fiber core C23 after having propagated through the GRIN lenses GRIN1 and GRIN2, i.e. the image of the fiber cores C11, C12, C13 is inverted at the fiber cores C21, C22, C23.

GRIN lenses are a good choice in backloadable versions of optical shape sensing technologies in medical interventional devices because of their compactness and their intrinsically low surface reflection. For, the light is not reflected or refracted at an air-glass transition but bent in a graded index profile extending, for example, in the radial direction of the GRIN lens. This property is used to eliminate all air to glass transitions when the connection is established, e.g. when the optical fiber, e.g. the optical fiber F1 and the GRIN lens GRIN1 are fusion spliced, glued or otherwise index-matched and pushed together. The reflection should be made low because otherwise it will overwhelm the relatively weak reflection signals coming from each point along the rest of the optical fiber F1. Between the connectors OC1 and OC2, a thin, index-matching foil IM may be arranged to reduce or eliminate reflection at the end facets OF1 and IF2.

FIG. 1 shows a typical length L of a GRIN lens of e.g. 1.3 mm and a typical diameter d thereof of e.g. 0.3 mm. A first short section of the optical fiber F1, for example 20-40 mm, starting just from the interface between the optical fiber F1 and the GRIN lens GRIN1 must be kept straight or at least in a known shape to know the starting direction as well as the starting position for the shape reconstruction of the fiber F1. In case of a backloadable guidewire, the connector OC1 including the GRIN lens GRIN1 and the proximal portion of the optical fiber F1 is therefore dimensioned as a rather stiff rod, and may be several centimeters long.

Figure 2:
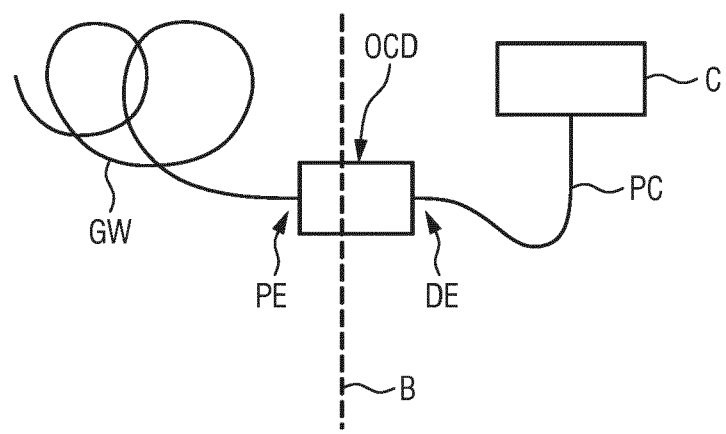
FIG. 2 shows a sketch of an arrangement of devices in a shape-sensing modality, with the working space schematically divided in a sterile zone on the left and a non-sterile zone on the right.

FIG. 2 shows a modality which is typical for minimally invasive medical procedures, which may include the use of a backloadable guidewire GW which is connected via an optical connection device OCD with a patch cord PC which in turn is connected to a console C. In case such a guidewire GW includes some optical fiber, for example for sensing or light delivery, the proximal end portion PE of the guidewire has the added functionality of being a connector like the connector OC1 in FIG. 1 and needs to mate with a counter connector, like the connector OC2 in FIG. 1, at a distal end portion DE of the patch cord PC. The guidewire GW which comes into direct contact with the patient must be sterile, while the patch cord and the console may not be sterile. The sterile zone also includes the connector of the guidewire GW at the proximal end PE, i.e. the connector of the guidewire must be sterile as well. When backloading a catheter on the proximal end of the guidewire and advancing it into the patient, the catheter must not being contaminated when pushed over the optical connector of the guidewire GW. In contrast, the optical connector at the distal end portion DE of the patch cord PC has not to be sterile and usually is non-sterile. Thus, a sterility barrier B is to be provided between both connectors, i.e. in or at the optical connection device OCD connecting the optical connectors OC1 and OC2 to one another. On the other hand, the optical connection between the optical connectors OC1 and OC2 should optically perform as best as possible for optimum optical signal transmission between them. The barrier B must be optically transparent and should have sufficiently low optical reflections (typically lower than −60 dB) and should transmit the light without introducing too much optical loss or aberration.

The purpose of an optical connection device OCD thus is to establish an optical connection, but also to form a sterile barrier between connectors of optical fiber devices, such as e.g. a guidewire GW and a patch cord PC. Such an optical connection device OCD may include a number of parts, which may be a drape or sock, a plug with an optical window, a clamp to hold the optical fiber devices together by transmission of a clamping force through the plug, and mechanics to provide alignment of the two optical fiber devices. In the following description the same reference numerals label the same or similar elements.

Figure 3:
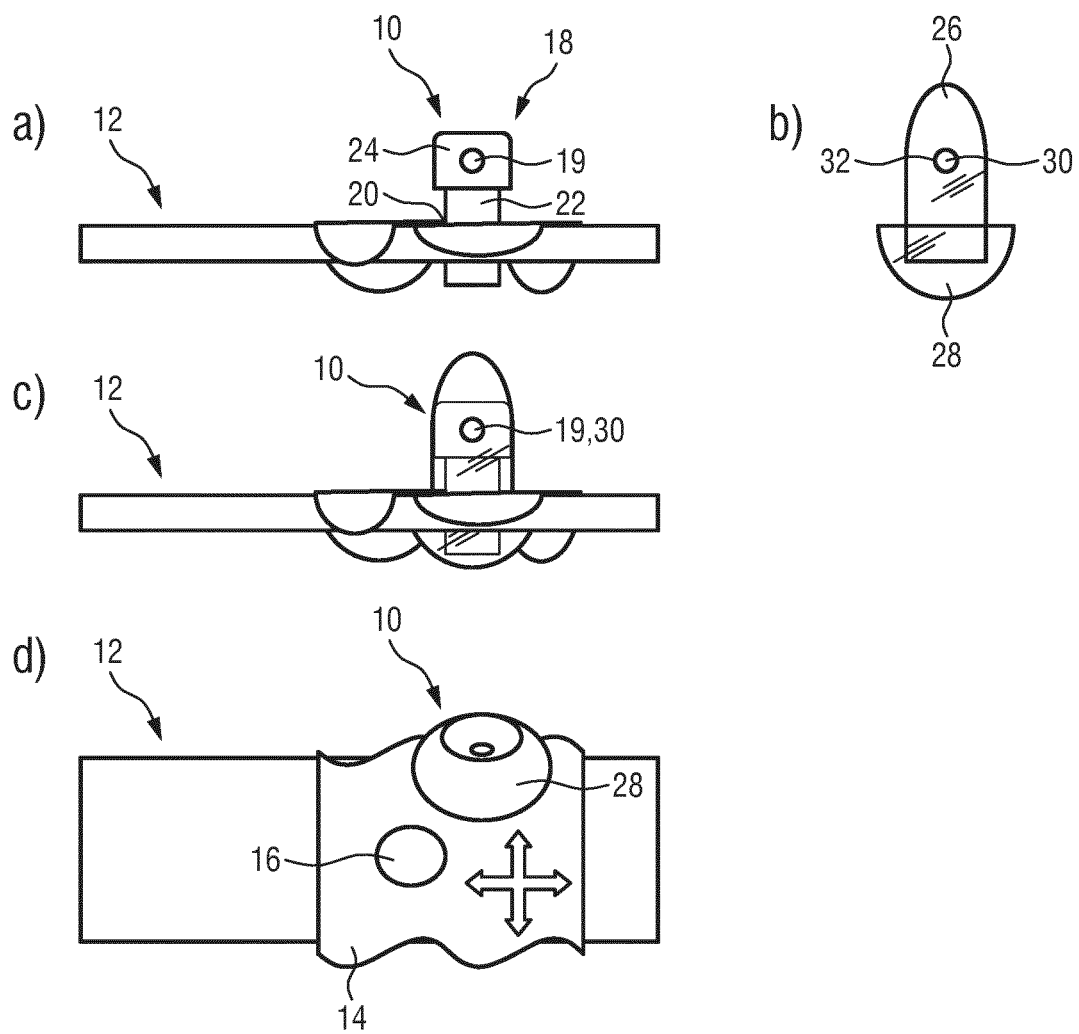
FIG. 3a) to d) schematically show an example of draping a clamp part of an optical connection device in a surgical environment, wherein FIGS. 3a) and 3c) show side views, FIG. 3d) shows a top view and FIG. 3b) shows a drape or sock in isolation in a side view.

With respect to FIGS. 3a) to d), a possible configuration of draping in connection with an optical connection device 10 is schematically shown. The optical connection device 10 is shown in FIGS. 3a), 3c) and 3d) without a plug part. FIGS. 3a) and 3c) show a side view of an operating or patient table 12 with an optical connection device 10 fixed thereto. Note that the drawings are not to scale. FIG. 3d) shows a top view of the operating table 12. FIGS. 3b), c) and d) show a drape 14 which covers part of a patient (not shown). Possible holes like hole 16 for performing surgery through hole 16 can be aligned with the patient and may be shifted independently from the position of the optical connection device 10. The optical connection device 10 is schematically shown with a clamp part 18 having a receptacle 24 with an opening 19 into which a plug part (not shown and to be described below) may be introduced for connection of a connector of a patch cord, for example. The drape 14 may, but advantageously may not, have a hole 20 through which a pole 22 of the optical connection device 10 may pass. Typically, the drape will fall down from the table around the pole 22, as shown in FIG. 3a), for attachment of the connection device 10 to the table 12. The clamp part 18 of the optical connection device 10 may be covered, for example before connecting the guidewire and the patch cord, with a sock 26 having a skirt 28 shown in FIG. 3b), wherein FIG. 3c) shows the sock 26 with skirt 28 covering the receptacle 24 of the clamp part 18 and pole 22. The sock 26 has a hole 30, the periphery of which may be reinforced by a grommet 32. When placed over the clamp part 18, the hole 30 matches with the opening 19 of the receptacle 24. The skirt 28 may go over the drape or it may go under the drape. Also a double-layered skirt may be used, the first layer going under the drape and the second layer going over the drape.

The drape 14, in particular the sock 26 with skirt 28 are embodiments of measures for providing a sterile connection between, for example, a guidewire connector and a patch cord connector via the optical connection device 10 as described herein.

Figure 4:
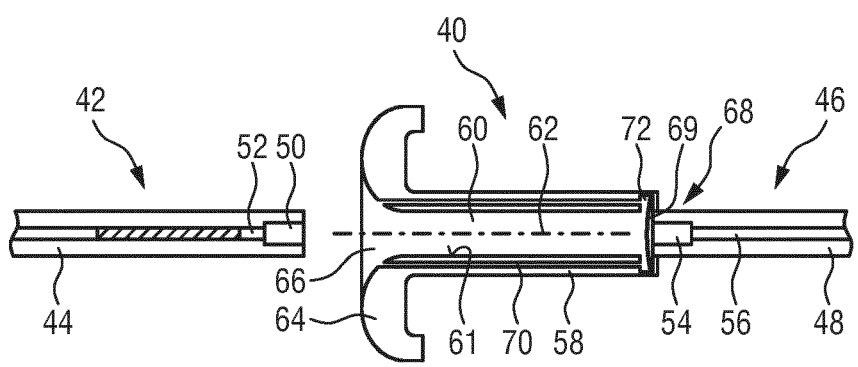
FIG. 4 schematically shows a longitudinal-sectional view of an embodiment of a plug part of an optical connection device together with connectors of optical fiber devices.

A plug part which may be used in optical connection device 10 is shown in FIG. 4. FIG. 4 shows an embodiment of a plug part 40 in a longitudinal section. FIG. 4 also shows a first connector 42 of a first optical fiber device 44 and a second connector 46 of a second optical fiber device 48. The first optical fiber device 44 may be a guidewire, and the second optical fiber device 48 may be a patch cord. Connector 42 includes a GRIN lens 50 and an optical fiber 52 fixedly connected thereto, and the connector 46 may comprise a GRIN lens 54 and an optical fiber 56 fixedly connected thereto.

The plug part 40 has a shaft 58 having a central lumen 60 (the neutral lumen) extending through the shaft 58 in longitudinal direction. The shaft 58 is elongated and has a shaft axis 62. The central lumen 60 is configured to receive the first connector 42. The plug part 40 further has a cap 64 which has an insertion opening 66 for insertion of the first connector 42 into the lumen 60. The first connector 42 is shown in FIG. 4 as being about to be slid into the lumen 60. An inner surface 61 of the lumen 60 serves as guiding surface for the connector 42.

The plug part 40 further comprises an optical window 68 which has a solid body element 69, for example a flexible, elastic transparent element, such as a foil, arranged longitudinally spaced apart from the first end of the shaft 58 at which the cap 64 is arranged. The second connector 46 is shown in FIG. 4 as it makes contact with the optical window 68 on a side opposite to the side of the window 68 facing the cap 64. The optical window 68 closes the interior of the shaft 58 including the lumen 60 against the environment. The second connector 46 may be spring loaded so that it gently pushes against the optical window 68 for good optical contact of the GRIN lens 54 with the optical window 68.

The plug part 40 further comprises one or more elongated channels 70 which is or are in fluid communication with the central lumen 60. In the embodiment shown in FIG. 4, fluid communication between the channel 70 and the lumen 60 is accomplished by a chamber 72 near the optical window 68. The optical window 68 thus does not hinder the fluid communication between the central lumen 60 and the channel 70. The channel or channels 70 has or have the function of equalizing pressure in the lumen 60 during insertion and retraction of the optical connector 42 and/or the optical connector 46. The chamber 72 also allows the optical window 68 to be pushed-in slightly by the connector 46.

The optical window 68 also functions as a sterile barrier between the connector 46 which may be non-sterile and the connector 42 which is sterile. The optical window 68 also ensures that any gas or fluid stays at the same side of the optical window 68.

In total, a sterility barrier is formed by the optical window 68 and the remaining parts of the plug part 40. Thus, the plug part 40 serves to improve sterility on the side of the optical connector 42.

The shaft 58 of the plug part 40 may be produced as an extruded part. In other embodiments, the cap 64 and the shaft 58 may be produced as one part by injection molding. In still other embodiments, the cap 64 may be produced by injection molding and then attached to the shaft 58. The optical window 68 may be attached to the shaft 58 during any of the afore-mentioned processes, in particular in an injection-molding process.

Figure 5:
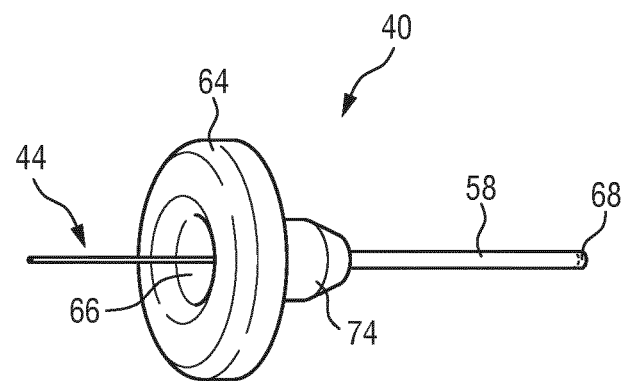
FIG. 5 shows a perspective view of an embodiment of a plug part of an optical connection device with a connector of an optical fiber device inserted into the plug.

FIG. 5 shows a plug part 40 in a perspective view, with a connector of an optical fiber device 44, e.g. a guidewire, inserted into the plug part 40. The plug part 40 comprises a shaft 58 having a lumen inside for receiving the connector part of the device 44. The connector of the device 44 thus cannot be seen in FIG. 5. The plug part 40 comprises a cap 64 similar to FIG. 4 except that the cap 64 has a protrusion or portion 74 which serves as a snap-fit or click part for snap-fit of the plug part 40 with a clamp as will be described later.

As shown in FIG. 5, the cap 64 may have a funnel or trumpet-shaped end comprising the insertion opening 66 which facilitates inserting the connector 42 into the plug part 40.

As can be seen in FIGS. 4 and 5, the cap 64 may have an outer diameter transverse to the shaft axis 62 which is larger by more than 5 times than the outer diameter of the shaft 58. For example, while the shaft 58 may have an outer diameter of about 1 to 4 mm, the cap 64 may have an outer diameter of about 1 cm to 5 cm, for example.

Figure 6:
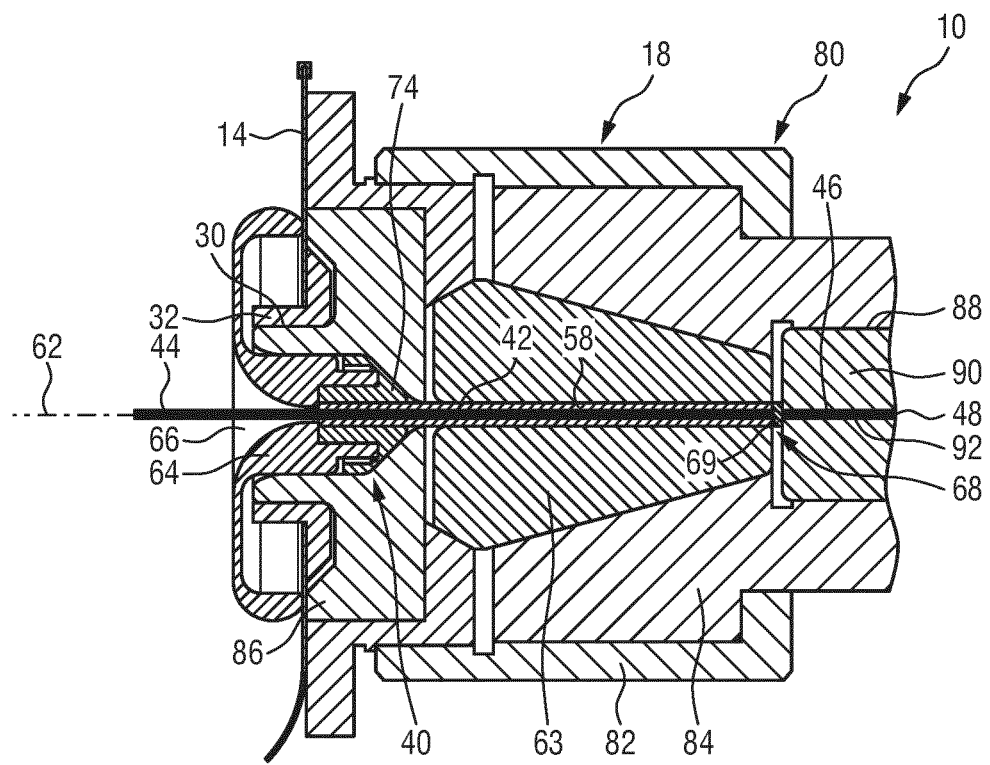
FIG. 6 shows a longitudinal-sectional view of an embodiment of an optical connection device with connectors of two optical fiber devices connected to each other.

FIG. 6 shows an optical connection device 10 with a plug part 40 and a clamp part 18 in a state where the plug part 40 and the clamp part 18 are connected with one another. A first connector 42 of a first optical fiber device 44 is shown inserted into the shaft 58 of the plug part 40, wherein the connector 42 is placed such that the outermost connector end of the connector 42 contacts the optical window 68. The clamp part 18 is configured such that it exerts a force onto the plug part 40, here onto the shaft 58 of the plug part 40, which deforms the plug part 40, in particular or only the shaft 58 when the clamp part 18 is tightened or closed. By deforming the shaft 58 of the plug part 40, the connector 42 is clamped and held in position and orientation with respect to the shaft axis 62 of the shaft 58 which is also the optical axis. In the example shown in FIG. 6 the clamp part 18 comprises a conical clamping part 63 which exerts the clamping force onto the shaft 58 of the plug part 40. However, other designs of clamping means can be used. The clamp part 18 further comprises a structure 80. The structure 80 comprises means for tightening (closing) and untightening (opening) the clamp part 18, which may be configured as a nut 82. The nut 82 co-acts with a coupler 84 which is configured to move relative to the conical part 63 in order to compress the clamping mouth 18 and thus the shaft 58 of the plug part 40 when the nut 82 is tightened. The structure 80 further has an abutment part 86 which is in threaded engagement with the nut 82. When the nut 82 is tightened, the nut pushes the coupler 84 in direction to the abutment part 86 thereby increasingly compressing the conical part 63.

The clamp part 18, here the structure 80 of the clamp part 18 is further configured to receive and hold the second connector 46 of the second optical fiber device 48, as shown in FIG. 6. For example, the coupler 84 may have a receiving bore 88 into which a holder 90 of the second connector 46 may be inserted and held therein. The holder 90 in turn has a receiving bore 92 for receiving and holding the second connector 46 in the holder 90. The second connector 46 is held in alignment with the shaft axis 62 of the shaft 58 of the plug part 40 so that the first and second connectors are in straight alignment along the optical axis as here defined by the shaft axis 62 when the connection between the connectors 42 and 46 is made by the optical connection device 10. The second connector 46 may slightly protrude from the receiving bore 92 in order to make a good optical contact with the optical window 68.

In the following, a method of optically connecting the first connector 42 of the first optical fiber device 44 with the second connector 46 of the second optical fiber device 48 is described. The method to be described may use the optical connection device 10 as shown in FIG. 6.

In a first step, the plug part 40 and the clamp part 18, with the second connector 46 of the patch cord 48 installed, are provided. Then, a sterile drape like the drape 14 or the socket 26 is applied over the clamp part 18. Next, the plug part 40 which may have been sterilized before, is inserted through the hole 30 reinforced with the grommet 32 of the drape 14. The cap 64 of the plug part 40 is larger than the hole 30 so that the cap 64 closes off the hole 30. In this way, the drape 14 makes a seal between the cap 64 and the clamp part 18. The cap 64 of the plug part 40 may be used as a handle when manipulating the plug part 40, in particular when inserting it into and removing it from the clamp part 18.

Due to the snap-fit portion 74 of the cap 64 of the plug part 40, the plug part 40 snaps or clicks into the clamp part 18. In this stage, the shaft 58 of the plug part sits in the conical compressible part of the clamp part 18. The end of the shaft 58 is in proximity to the window 68 in this stage. The clamp part 18 may be slightly tightened in this stage, in the embodiment of FIG. 6 by screwing the nut 82 a little bit further onto the abutment part 86 until the plug part 40 is caught in the clamp part 18. Hereafter, the connector 42 of the optical fiber device 44 may be inserted through the insertion opening 66 of the cap 64 into the lumen 60 (FIG. 4) of the shaft 58 of the plug part 40. Then, the clamp part 18 may be tightened further, but only so much that the connector 42 may still slide and may be rotated about the shaft axis 62 in the lumen 60. The connector 42 is pushed all the way down the lumen 60 until the connector end contacts the window 68, so that for example a proper optical signal is found from the central core of the optical fiber of the optical fiber device 44 (see FIG. 1). Then the connector 42 is secured in place by further tightening the clamp part 18 adequately. Rotational alignment of the outer fiber cores (see FIG. 1) of the connector 42 with respect to the connector 46 may be done from either side, i.e. by rotating the optical fiber device 44 or the optical fiber device 48. In the example shown in FIG. 6, it is preferable to rotate the second optical fiber device 48, e.g. a patch cord, until optimum signal coupling between the connectors 42 and 46 is found.

When the proper rotational alignment between the connectors 42 and 46 is found by rotation of connector 42, the clamp part 18 is further tightened so as to clamp and hold the first connector 42 in position and orientation with respect to the second connector 46, which is also an alignment with the shaft axis 62 of the shaft 58 of the plug part 40.

When the proper rotational alignment between the connectors 42 and 46 is to be found by rotation of connector 46, the clamp part 18 must be further tightened beforehand so as to clamp and hold the first connector 42 in position and orientation with respect to the second connector 46, which is to be rotated by rotating the holder 90 in which it is held.

Per medical procedure, or per patient, it is possible to use only one sterile plug part 40. Removing the plug part 40 would temporarily break the sterile barrier. One plug part 40 can be used with several optical fiber devices and exchanged before it wears out.

In the method described before, the second connector 46 is inserted into the clamp part 18 beforehand, i.e. before the plug part 40 is inserted into the clamp part 18. The second connector 46 (and thus the second optical fiber device 48) may be connected to the clamp part 18 even before bringing the clamp part 18 into a surgical theater.

It is to be noted that FIG. 6 shows an example of a design of the clamp part 18, and other designs can be envisaged. Independent on the actual design of the clamp part 18, the clamp part 18 preferably holds the first connector 42, which may be the connector of a guidewire, rather straight in order to give it a well-defined direction from which shape reconstruction of the guidewire in an optical shape sensing procedure can start.

Preferably, the clamp part 18 and the plug part 40 have a rotational symmetry about the longitudinal axis (axis 62) so that the connector 42 is not displaced when the clamp part 18 is tightened.

As described above, the first connector 42 is clamped in the plug part 40 by a deformation of the plug part 40, in particular the shaft 58 thereof, wherein the deformation is imparted to the plug part 40 by the clamp part 18 when the latter is tightened. Elastic deformation of the plug part 40 is preferable. Any plastic, i.e. inelastic or permanent deformation of the plug part 40 should be limited such that repeated clamping and unclamping is possible with the same plug part 40, without breaking the sterile barrier. The material of the plug part 40 should be sufficiently smooth to let the first connector slide-in easily, but, when the clamp part 18 is tightened and the plug part 40 is compressed onto the connector 42, the connector 42 should find sufficient friction with the material of the plug part 40.

Figure 7:
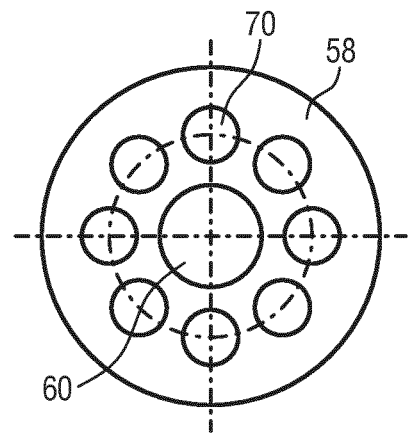
FIG. 7 shows a cross-sectional view of a shaft of a plug part of an optical connection device according to an embodiment.

FIG. 7 shows another embodiment of shaft 58 of the plug part 40 in a cross-sectional view. As described above, the shaft 58 may have one or more channels 70 in fluid communication with the central lumen 60 of the shaft 58. Fluid communication may be accomplished via the chamber 72 as shown in FIG. 4. In the embodiment in FIG. 7, there are eight such channels 70 which surround the central lumen 60 in an angularly distributed, in particular angularly equidistant manner around the lumen 60. Note that the shaft 58 is shown in FIG. 7 in an exaggerated scale. The outer diameter of the shaft 58 may be as small as a few mm, for example about 2 mm. The central lumen 60 may have an inner diameter of about 1 mm or less, typically 0.035 inch (0.889 mm), 0.018 inch (0.46 mm) and 0.014 inch (0.36 mm), and the channels 70 may have an inner diameter of about 0.5 mm.

Figure 8:
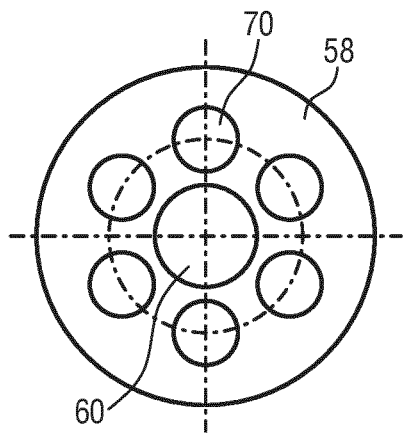
FIG. 8 shows a cross-sectional view of a shaft of a plug part of an optical connection device according to an embodiment.

FIG. 8 shows another embodiment of the shaft 58 with six channels 70 surrounding the central lumen 60 in angularly distributed manner. A plug part 40 with six channels 70 may be advantageous when increasing the compression force imparted by the clamp part 18 on the plug part 40, because the onset of plastic deformation in some parts of the plug part 40 is at a larger force relative to the force required for clamping the connector 42 in the shaft 58. Hence, the tolerance on the applied force is improved. This also depends somewhat on the material used for the plug part 40, in particular the shaft 58, but it is mainly a geometrical effect due to the design of position and diameter of the channels 70. In particular, in an example, six channels with inner diameter of 0.58 mm for a 3 mm diameter shaft 58 may surround central lumen 60 of 0.91 mm.

Figure 9:
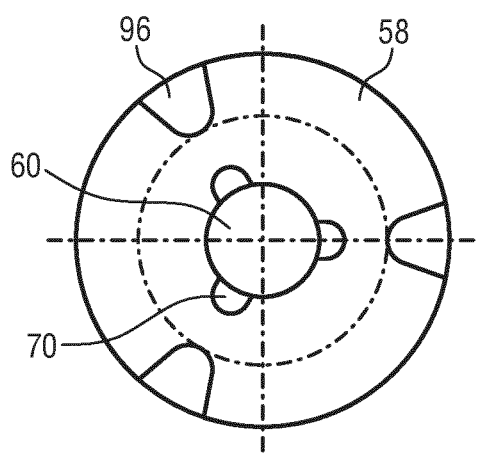
FIG. 9 shows a cross-sectional view of a shaft of a plug part of an optical connection device according to an embodiment.

A further embodiment of the shaft 58 is shown in FIG. 9. In this embodiment, the channels 70 surround the central lumen 60 and communicate with the lumen 60 over at least part of their length along the lumen 60. In other words, in this embodiment, the channels 70 are part of the lumen 60. Such a configuration is advantageous in terms of manufacturing the plug part 40 or the shaft 58 by injection molding. For better mechanical compliance, the outer periphery of the shaft 58 may have indentations 96.

It is preferred, if the inner diameter of the central lumen 60 of the shaft 58 of the plug part 40 fits to the outer diameter of the connector 42 even before the plug part 40 is compressed by the clamp part 18, i.e. the inner diameter of the central lumen 60 approximately corresponds to the outer diameter of the connector 42 in the uncompressed state of the plug part 40. However, as mentioned above, in the uncompressed state of the plug part 40, the connector 42 should be smoothly slidable in the lumen 60.

Figure 10:
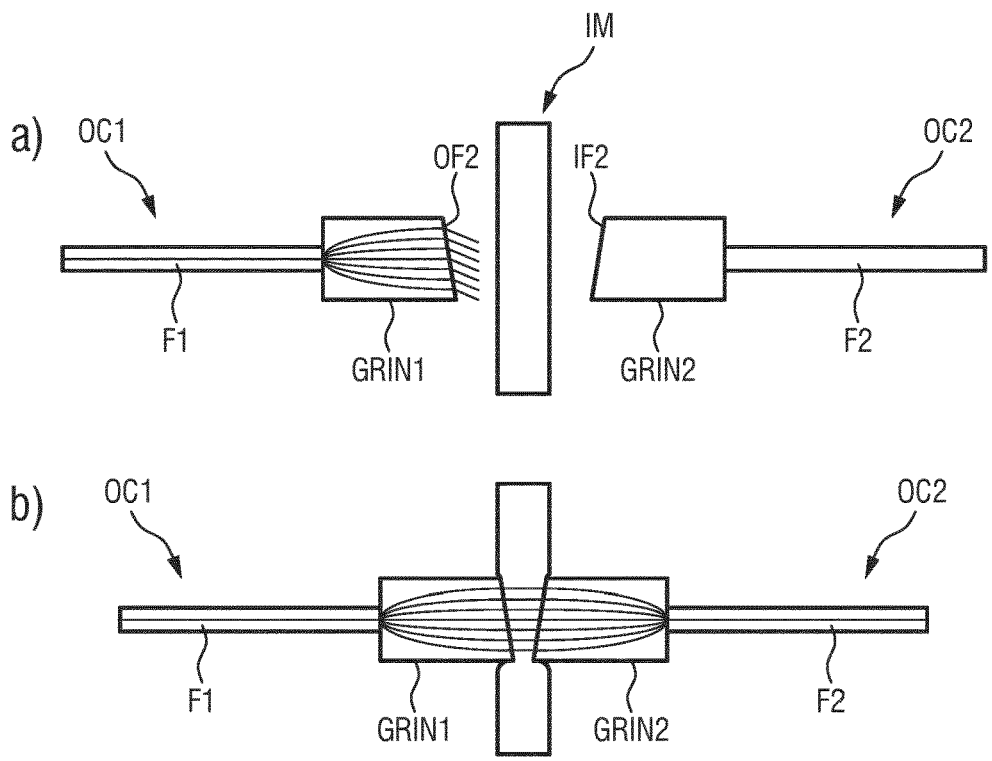
FIGS. 10a) and b) schematically show two connectors with a transparent element therebetween.

When bringing the connectors 42 and 46 together as shown in FIG. 6, with the optical window 68 in between, some air gap may remain that will cause optical reflection and also may cause refraction. This will be explained with reference to FIGS. 10a) and 10b). FIGS. 10a) and 10b) show, similar to FIG. 1, the connectors OC1 and OC2 with GRIN lenses GRIN1 and GRIN2 and optical fibers F1 and F2, respectively, before the connectors OC1 and OC2 are pushed together. FIG. 10a) shows a small but inevitable angle of end facet OF1 and end facet IF2 which may be the result from a polishing process of the connector ends of connector OC1 and connector OC2. Such angles of the connector end OF1 may result in that light from the single fiber cores of the optical fiber F1 exit the GRIN lens GRIN1 not parallel to the optical axis, but under an angle thereto. Similar aberrations may occur at the connector end IF2 of optical connector OC2. The problem increases, if the geometry of the connector end OF1 is different from the geometry of connector end IF2 as shown in FIGS. 10a) and 10b).

In order to overcome the geometrical differences between the connector ends OF1 and IF2, a refractive-index matching transparent element IM is placed between the optical connectors OC1 and OC2. The transparent element IM should be sufficiently thick and sufficiently compressive so that, when pushing the connectors OC1 and OC2 together, the transparent element IM is deformed and thus compensates for the geometrical differences between the connector ends OF1 and IF2, and due to the index matching property of the transparent element IM, any optical aberrations due to the geometrical differences between the connector ends are eliminated. Such a transparent element IM is preferably used as the optical window 68 in the optical connection device 10 as shown in FIG. 6 and as shown in FIG. 4 for the plug part 40 of the optical connection device 10.

As described herein, the method of optically connecting the connector 42 and 46 with one another may comprise inserting the plug part 40 into the clamp part 18, and pre-tightening the clamp part 18 until it is in contact with the plug part 40. The method may further comprise inserting the connector 42 of the first optical fiber device 44 down into the lumen 60 of the shaft 58 of the plug part 40. By tightening the clamp part 18 further by a given amount of displacement, the plug part 40 is compressed and elastically deformed. When the first connector 42 is inserted into the lumen 60 of the plug part 40, the force exerted by the clamp part 18 should be at a force level which allows sliding of the connector 42 in the shaft 58, in particular such that the connector 42 can still be rotated about the shaft axis 62. The force level for the final clamping of the connector 42, i.e. for providing sufficient friction to hold the connector 42 against the inner guiding surface of the shaft 58 is higher, accordingly.

For example, if a linear elastic material behavior of the material of the shaft 58 is assumed, the mechanical behavior of the cross-sectional geometry of the shaft 58 of the plug part 40 as shown in FIGS. 7 and 8 may be as follows: The contact force per length at plastic deformation (minimal clearance) is 12.6 N/mm. If a friction coefficient of 0.3 for the material PEBAX 5533 on steel is assumed, the pull-out force per length equals 3.8 N/mm. When the total clamping length is approximately 30 mm, the total force is 114 N, while approximately 5 N is needed (corresponding to a load of 500 g for holding the connector 42 in the plug part 40 by friction). A contact force of 0.55 N/mm is required which is, thus, much less than the contact force per length at which plastic deformation would occur. It was experimentally found that the clamp part 18 in cooperation with the plug part 40 holds the connector 42 very well. Note however that in reality the friction coefficient may be significantly lower than 0.3 N/mm and that the clamping force may be higher than indicated above.

Figure 11:
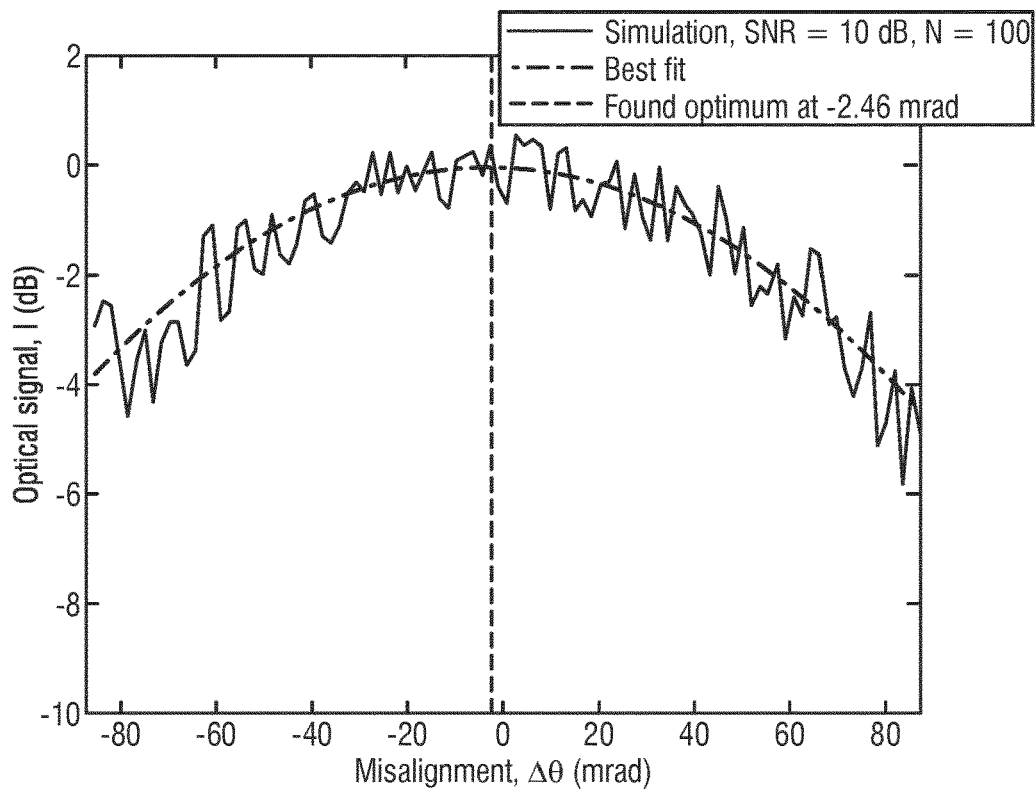
FIG. 11 shows a graph of a simulation of an optical signal on outer cores of multi-core optical fibers as function of a misalignment of the outer cores.

In the method described above, proper alignment of the connector 42 and the connector 46 with respect to one another is essential for a good optical performance of the optical connection device 10. A procedure for alignment of the connectors 42 and 46 with respect to one another can be performed as follows. When inserting the connector 42 into the plug part 40, the connector 42 is slid down to the bottom, i.e. to the window 68 until an optical signal on the central core of the optical fiber of the connector 42 is received. Then, either the second optical fiber device 48 (and thus the second connector 46) and/or the first optical fiber device 44 (and thus the first connector 42) are rotated about the optical axis (axis 62) and the optical signals on the outer cores of the optical fiber of the first and second optical fiber devices are monitored. Once a signal is detected on the outer cores, the device 44 and/or the device 48 are rotated further across the optimal orientation in total over a range of $\theta_{range}$ centered around the optimal position. Further, the optical signal on the outer cores is then analyzed as a function of angle to find the optimal orientation. FIG. 11 shows a simulation of an optical signal on the outer cores as a function of the misalignment for a system with a signal-to-noise ratio (SNR) of 20 dB, a mode field diameter of 6 µm, and a geometrical distance of the outer core from the fiber center at 35 µm. In this case, the limited SNR causes the algorithm to find the optimum at −2.46 mrad, while it is actually at 0 mrad.

After analyzing the optical signal on the outer cores, the optical fiber device 44 and/or the optical fiber device 48 are rotated back to the calculated optimal position. The aforementioned procedure may be performed using the optical console C in FIG. 2.

For extra accuracy, at each afore-mentioned step, a polarization balancing procedure may be applied.

Figure 12:
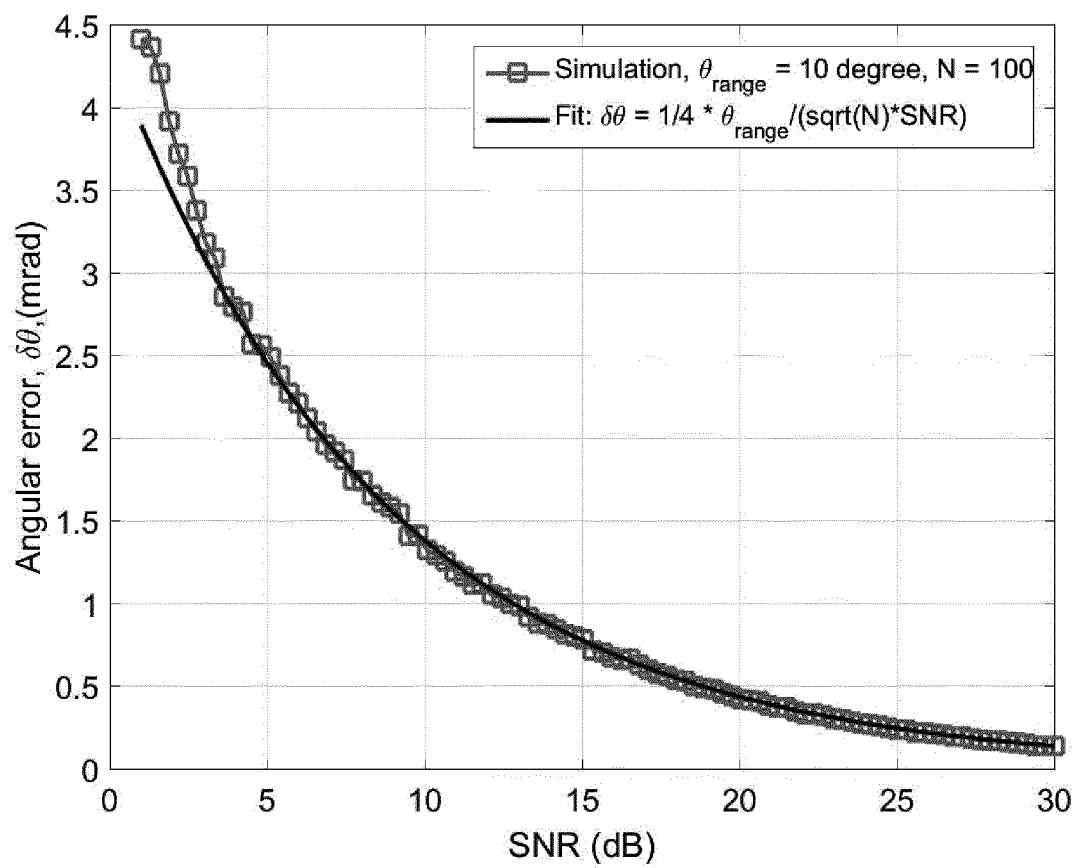
FIG. 12 shows a graph of a simulation of an angular error one makes in estimating the optimal position of the outer cores of multiple-core optical fibers as function of the available signal-to-noise ratio.

For the accuracy δθ with which the optimal orientation may be determined, holds $$\delta\theta \propto \theta_{range}/(SNR \cdot N^{1/2}),$$

where $\theta_{range}$ is the range over which the scan is performed, N is the number of measurements within this range, and SNR is the signal-to-noise ratio. FIG. 12 shows a simulation of an optical signal on the outer cores as function of the available SNR. For each point, the simulation was run 1000 times. This simulation shows that an accuracy in the order of mrads should be feasible with sufficient SNR and measurement points. The accuracy might be further improved by using the optical signals on all three outer cores of the optical fibers to determine the optimal position.

For rotating the first connector 42 relative to the second connector 46 or rotating the second connector 46 relative to the first connector, a mechanical rotation mechanism (not shown) may be provided which may rotate the corresponding connector under optical feedback control using the optical signals on one of or all the outer cores of the optical fibers to adjust the optimal position.

The transparent element of the optical window 68 preferably is elastic and has sufficient strength. Further, preferably, the transparent element has a refractive index that matches that of the GRIN lenses of the connectors 42 and 46. Further preferably, the transparent element has sufficient thickness, for example 20-400 µm, typically 80 µm. The transparent element further should be transparent to the used wavelength, for example in a shape sensing procedure. The transparent element may be hermetically attached to the plug part 40, e.g. by heat sealing or using adhesives. Further, the transparent element of the optical window 68 preferably is sterilizable.

Suitable materials for the transparent element of the optical window 68 are a polyester/acrylic development product from Amcor (B), ethylene-vinylacetate copolymer, methyl-phenyl silicone, poly-ethylmethacrylate. The transparent element may also be made of a layer structure from different materials to meet the different mechanical properties (strength and flexibility) easier. In this case, the different materials should have the same refractive index.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An optical connection device for optically connecting a first connector of a first optical fiber device with a second connector of a second optical fiber device along an optical axis, the optical connection device comprising:

a plug part having an elongated shaft having a longitudinal shaft axis and a lumen extending through the shaft along the shaft axis for receiving the first connector, the plug part further having a cap at a first end of the shaft which has an insertion opening for insertion of the first connector into the lumen, the opening being aligned and communicating with the lumen, the plug part having an optical window having a solid body element which closes an interior of the shaft including the lumen against an environment, wherein an end of the first connector contacts the optical window when the first connector is inserted into the lumen, wherein the plug part is at least in part deformable; and a clamp part, wherein the plug part is configured to be at least partially inserted into the clamp part, and the clamp part is configured to, when the plug part is at least partially inserted in the clamp part and when the first connector is inserted into the lumen of the shaft of the plug part, exert a force onto the plug part which deforms the plug part upon tightening the clamp part so as to clamp and hold the first connector in position and orientation with respect to the optical axis.

2. The optical connection device of claim 1, arranged to cooperate with a drape or sock having a hole and configured to be arranged over the clamp part, wherein the shaft of the plug part is configured to be insertable through the hole into the clamp part.

3. The optical connection device of claim 2, wherein the cap of the plug part and the clamp part are configured to be sealed by the drape or sock when arranged between the cap and the clamp part.

4. The optical connection device of claim 1, wherein the lumen of the shaft is arranged centrally in the shaft, and wherein the shaft has at least one elongated channel in fluid communication with the lumen.

5. The optical connection device of claim 4, wherein the shaft has a plurality of channels in fluid communication with the lumen and arranged angularly distributed around the lumen.

6. The optical connection device of claim 1, wherein the shaft of the plug part is elastically deformable.

7. The optical connection device of claim 1, wherein the solid body element of the optical window comprises a transparent element having a refractive index that is matched with a refractive index of at least one of a first optical element of the first connector and a second optical element of the second connector.

8. The optical connection device of claim 1, wherein the solid body element of the optical window comprises a transparent element which is elastically deformable in longitudinal direction of the lumen.

9. The optical connection device of claim 1, wherein the cap of the plug part has a portion configured to be snap fitted into the clamp part.

10. The optical connection device of claim 1, wherein the cap of the plug part has a funnel or trumpet shaped end comprising the insertion opening.

11. The optical connection device of claim 1, wherein the optical connection device is configured to allow rotation of the first connector, when inserted into the plug part, relative to the plug part about the shaft axis before the clamp part is tightened.

12. The optical connection device of claim 1, wherein the shaft of the plug part has an inner guiding surface which allows sliding of the first connector in the shaft when the clamp part is not tightened, and which provides friction to hold the first connector in place when the clamp part is tightened.

13. The optical connection device of claim 1, further comprising a structure configured to connect and hold the second connector of the second optical fiber device to the clamp part.

14. A method of optically connecting a first connector of a first optical fiber device with a second connector of a second optical fiber device, the method comprising:

providing a plug part having an elongated shaft with a lumen extending through the shaft, a cap at a first shaft end of the shaft which has an insertion opening, the opening being aligned and communicating with the lumen, the lumen having an optical window having a solid body element which closes an interior of the shaft including the lumen against an environment;

providing a clamp part having the second connector connected thereto;

inserting the plug part at least partially into the clamp part so that the optical window contacts the second connector at one side of the optical window;

inserting the first connector into the plug part so that the first connector contacts the optical window at an opposite side of the window; and tightening the clamp part to exert a force onto the plug part so as to deform the plug part to clamp the first connector and to hold the first connector in position and orientation with respect to the second connector.

15. The method of claim 14, further comprising, before tightening the clamp part, rotationally aligning the first connector and the second connector with respect to one another while measuring an optical signal passed through the first and second connectors.

16. The optical connection device of claim 1, wherein the optical connection device is configured to allow rotation of the second connector relative to the first connector when it is positioned and after the clamp part is tightened.

17. The optical connection device of claim 1, wherein the first connector comprises a first graded index (GRIN) lens and a first optical fiber connected to the first GRIN lens, and the second connector comprises a second GRIN lens and a second optical fiber connected to the second GRIN lens.

18. The optical connection device of claim 17, wherein the first GRIN lens faces the second GRIN lens when the first connector is inserted into the lumen of the shaft of the plug part, wherein each of the first GRIN lens and the second GRIN lens is in contact with opposite sides of the optical window.

19. The optical connection device of claim 18, wherein the optical window comprises a transparent element having a refractive index that matches refractive indices of the first and second GRIN lenses.

20. The method of claim 14, wherein the first connector comprises a first graded index (GRIN) lens and a first optical fiber connected to the first GRIN lens, and the second connector comprises a second GRIN lens and a second optical fiber connected to the second GRIN lens, such that when the first connector is inserted in the plug part, the first GRIN lens is aligned with the second GRIN lens on the opposite side of the optical window.

* * * * *